United States Patent [19]
Fischell et al.

[11] Patent Number: 5,749,825
[45] Date of Patent: May 12, 1998

[54] MEANS METHOD FOR TREATMENT OF STENOSED ARTERIAL BIFURCATIONS

[75] Inventors: Robert E. Fischell, Dayton, Md.; David R. Fischell, Fair Haven, N.J.; Tim A. Fischell, Richland, Mich.; Todd H. Turnland, Sunnyvale, Calif.

[73] Assignee: IsoStent, Inc., Belmont, Calif.

[21] Appl. No.: 714,315

[22] Filed: Sep. 18, 1996

[51] Int. Cl.⁶ .................................................. A61N 5/00
[52] U.S. Cl. ............................ 600/3; 606/194; 623/12
[58] Field of Search .................. 600/1–8; 623/1, 623/12; 606/191–92, 194–95, 197–98

[56] References Cited

U.S. PATENT DOCUMENTS

| | | | |
|---|---|---|---|
| 5,176,617 | 1/1993 | Fischell et al. | 600/3 |
| 5,609,627 | 3/1997 | Goicoechea et al. | 606/194 |
| 5,632,763 | 5/1997 | Glastra | 606/194 |
| 5,639,278 | 6/1997 | Derume et al. | 623/12 |

*Primary Examiner*—John P. Lacyk

[57] ABSTRACT

A stent delivery catheter system for the treatment of stenoses at an arterial bifurcation consists of a main guide wire, a side branch guide wire, a unique design balloon angioplasty catheter which includes a side branch tube and a stent that can be deployed to a larger diameter in the main artery leading to the arterial bifurcation, and deployed to a smaller diameter within one of the branch arteries at an arterial bifurcation. The balloon angioplasty catheter used to deploy the dual diameter stent has a proximal section that has a larger diameter as compared to the diameter of a distal section which distal section is designed to be placed in a branch artery of the bifurcation. An opening in the wall of the stent allows for the passage of the side branch tube that provides angular orientation of the pre-deployed stent relative to the two branches of the bifurcation. The side branch tube is also used to help assure proper longitudinal placement of the stent relative to the saddle point of the bifurcation. After the stent is deployed, the opening in the stent wall allows unobstructed blood flow into that side branch artery that is not initially stented.

19 Claims, 5 Drawing Sheets

5,749,825

MEANS METHOD FOR TREATMENT OF STENOSED ARTERIAL BIFURCATIONS

FIELD OF USE

This invention is in the field of intravascular stents designed to maintain vascular patency.

BACKGROUND OF THE INVENTION

Intravascular stents are now frequently used for the treatment of arterial stenoses. However, no extant stent is ideally suited for the treatment of arterial stenoses at the site of an arterial bifurcation. One reason why present stents are not ideally suited is because they deploy to a uniform diameter which is not suitable for arterial bifurcations which have a larger diameter main artery and smaller diameter branch vessels. Furthermore, present stents do not have an appropriate opening in the wall of the cylindrical stent structure to allow free blood flow into a side branch after the stent is deployed.

Still further, existing stents are not designed for easy and precise longitudinal placement at the site of an arterial bifurcation.

SUMMARY OF THE INVENTION

A stent delivery catheter system (including the stent itself) for the treatment of stenoses at an arterial bifurcation consists of a main guide wire, a side branch guide wire, a unique design balloon angioplasty catheter which includes a side branch tube and a stent that can be deployed to a larger diameter in the main artery leading to the arterial bifurcation, and deployed to a smaller diameter within one of the branch arteries at an arterial bifurcation. The balloon angioplasty catheter used to deploy the dual diameter stent has a proximal section that has a larger diameter as compared to the diameter of a distal section which distal section is designed to be placed in a branch artery of the bifurcation. An opening in the wall of the stent allows for the passage of the side branch tube that provides angular orientation of the pre-deployed stent relative to the two branches of the bifurcation. The side branch tube is also used to help assure proper longitudinal placement of the stent relative to the saddle point of the bifurcation. After the stent is deployed, the opening in the stent wall allows unobstructed blood flow into that side branch artery that is not initially stented. After the bifurcation stent is properly placed and deployed, a second stent can be used to open the side branch that is not stented by the bifurcation stent.

Therefore, it is an object of this invention to provide a stent delivery catheter system that is ideally suited for stent placement at the site of an arterial bifurcation.

Another object of this invention is to utilize a side branch tube adapted to be advanced over a guide wire placed into a side branch artery in order to properly place the pre-deployed stent both as to its angular orientation relative to the side branch artery and also its longitudinal position relative to the saddle point of the bifurcation.

Still another object of this invention is to have a bifurcation stent whose pre-deployed outside diameter when mounted on a balloon of a balloon angioplasty catheter is less than 2.0 mm.

Still another object of this invention is to have an opening in the wall of the stent through which the side branch tube is placed prior to deployment and through which unimpeded blood flow into one side branch is obtained after stent deployment.

Still another object of this invention is to disclose and teach a method for using the combination of a main guide wire, a side branch guide wire and a side branch tube attached to an inflatable balloon to provide proper angular orientation and longitudinal positioning of a bifurcation stent prior to stent deployment.

These and other important objects and advantages of this invention will become apparent from the detailed description of the invention and the associated drawings provided herein.

DETAILED DESCRIPTION OF THE INVENTION

Figure 1:
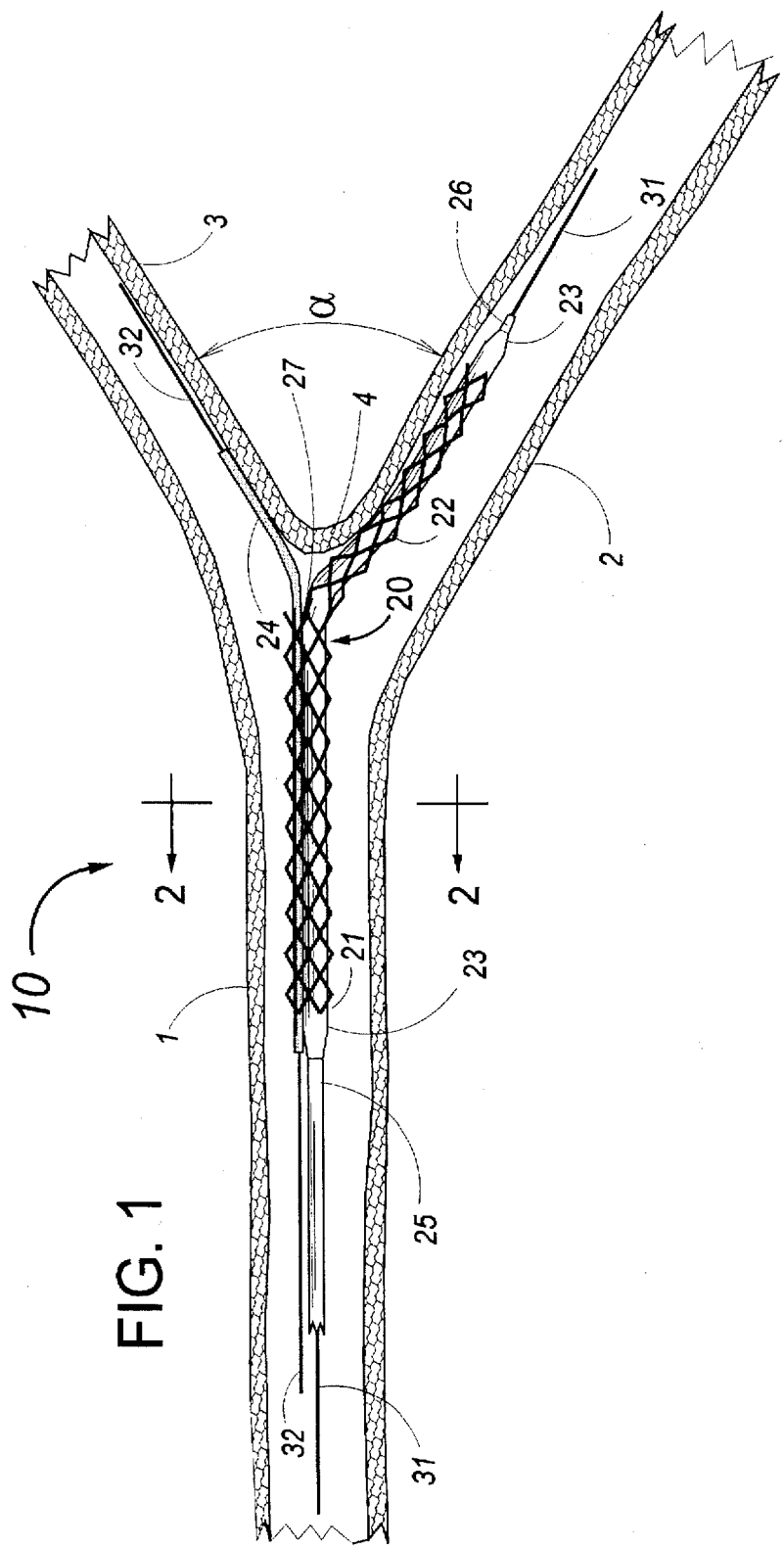
FIG. 1 is a longitudinal cross section of a distal portion of a stent delivery catheter system for stenting an arterial bifurcation as shown in its pre-deployed configuration.

FIG. 1 shows a distal portion of a stent delivery catheter system 10 which system includes a pre-deployed stent 20 having a proximal portion 21 and a distal portion 22. The stent 20 is mounted on a balloon 23 which is sealingly joined at its proximal end to the distal end of an outer shaft 25. The balloon 23 is sealingly joined at its distal end to the distal end of an inner shaft 26. This design is typical of balloon angioplasty catheters that are well known in the art of devices used by interventional cardiologists and radiologists.

Figure 2:
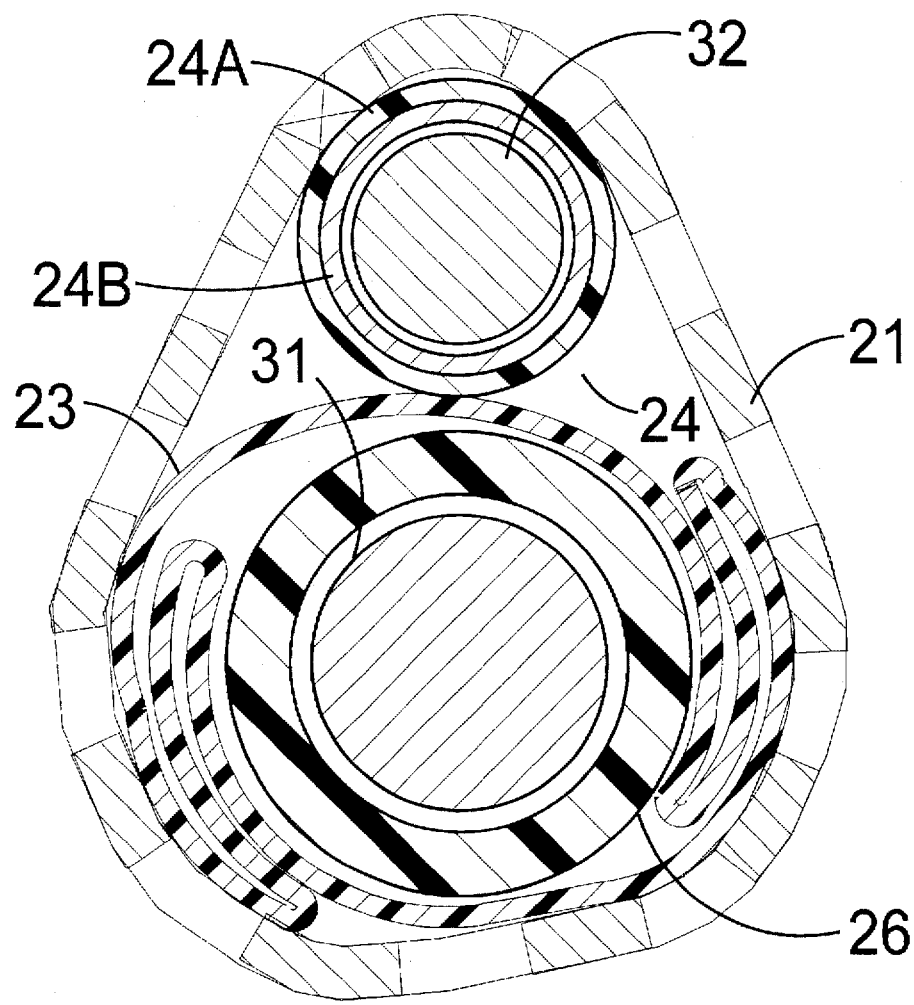
FIG. 2 is a highly enlarged cross section of the stent delivery catheter system at section 2—2 of FIG. 1.

FIGS. 1 and 2 show the stent proximal portion 21, the balloon 23, a side branch tube 24 mounted onto the outer surface of the balloon 23, a side branch guide wire 32, and a main guide wire 31 that is adapted to pass through the inner shaft 26. FIG. 1 also shows the stent distal portion 22 and a main artery 1 which continues distally as a main artery continuation 2. The artery continuation 2 and a side branch artery 3 form a bifurcation at the distal end of the main artery 1. The point where the arteries 2 and 3 intersect can be defined as the saddle point 4. It is important to note from FIG. I how the saddle point 4 causes the crotch point 27 to be properly positioned both as to the angular orientation of the stent 20 and longitudinal placement relative to the arterial bifurcation. The angle α in FIG. 1 can be defined as the bifurcation angle.

Figure 3:
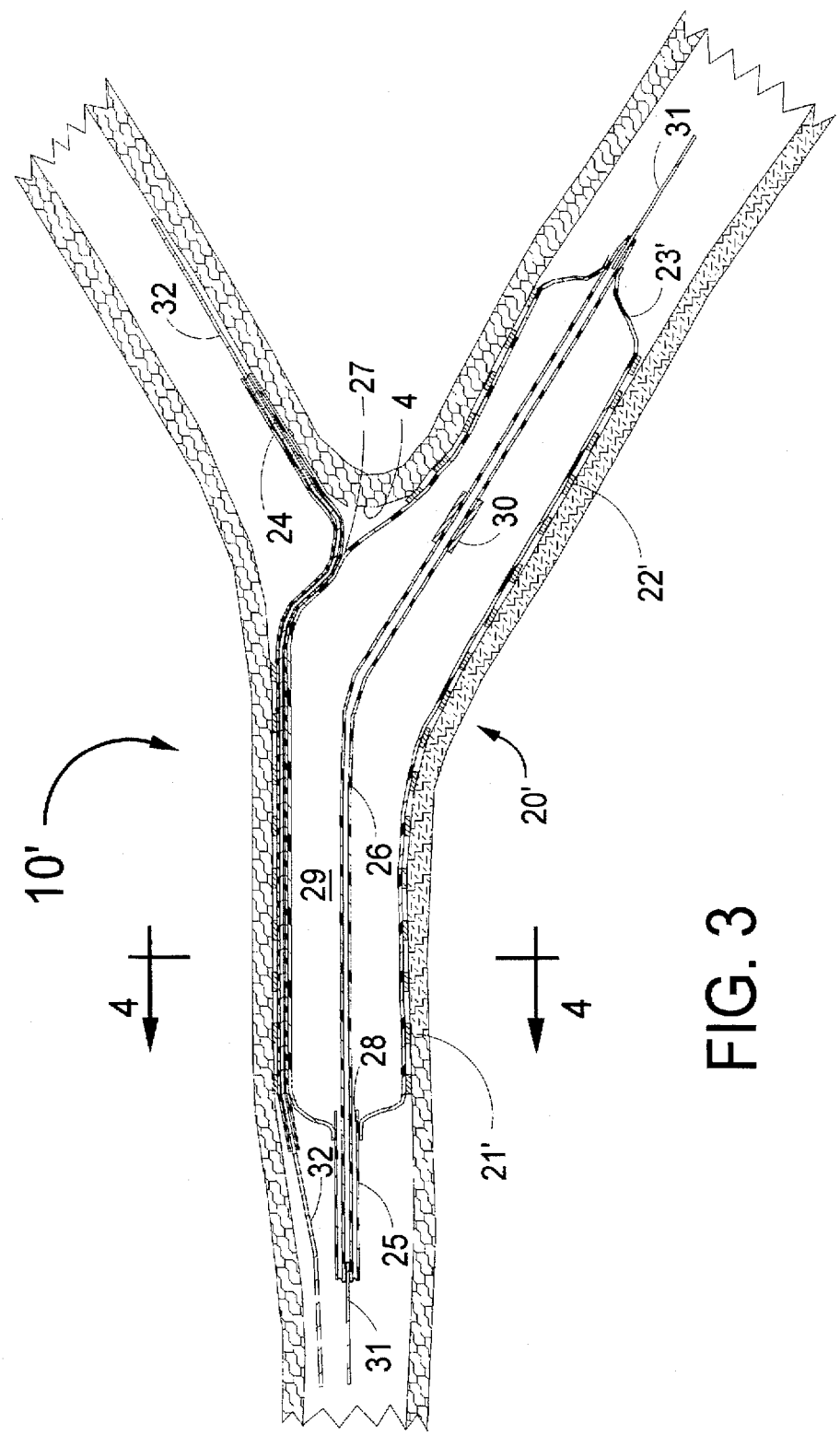
FIG. 3 is a longitudinal cross section of a distal portion of a stent delivery catheter system for stenting an arterial bifurcation as shown in its deployed configuration.
Figure 4:
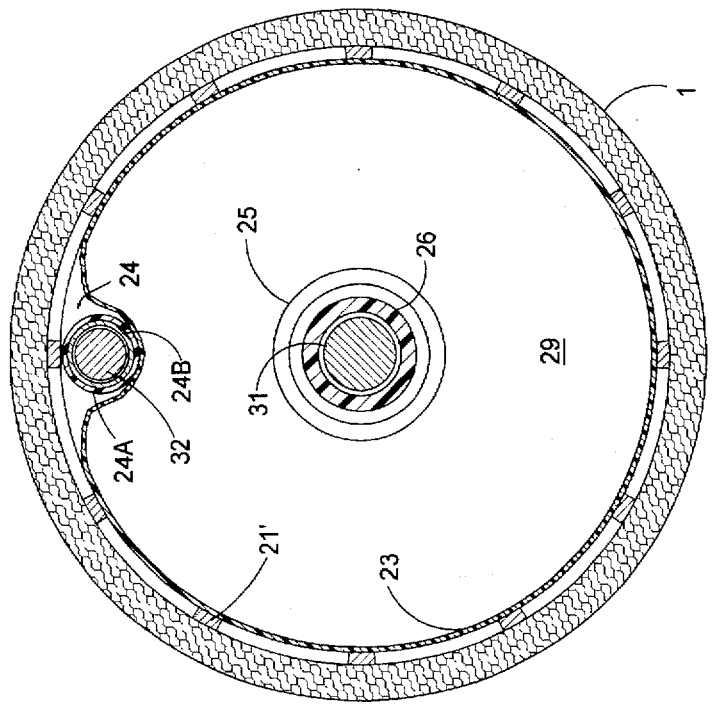
FIG. 4 is a highly enlarged cross section of the stent delivery catheter system at section 4—4 of FIG. 3.

FIG. 3 illustrates the stent delivery catheter system 10' with a deployed stent 20' including the stent distal portion 22', shown on the inflated balloon 23'. FIGS. 3 and 4 show the deployed stent proximal portion 21', the inner shaft 26 advanced over the main guide wire 31, and the side branch tube 24 advanced over the side branch guide wire 32. FIG. 3 also shows the distal end of the inflated balloon 23' sealingly joined (typically with adhesive) to the distal end of the inner shaft 26 and the proximal end of the inflated balloon 23' which is sealingly joined to the distal end of the outer shaft 25. An annular passageway 28 allows fluid to be inserted into or removed from the interior chamber 29 of the balloon 23'. A radiopaque marker band 30 mounted on the inner shaft 26 is used with fluoroscopy to help obtain accurate longitudinal positioning of the stent delivery catheter system 10'. It is important to note from FIG. 3 how the saddle point 4 causes the crotch point 27 to be properly positioned both as to the angular orientation of the stent 20' and longitudinal placement relative to the arterial bifurcation. Although the side branch tube 24 ideally extends distally beyond the crotch point 27 by 10 to 50 mm, a continuation as short as 1.0 mm beyond the crotch point 27 could also be used.

FIGS. 2 and 4 show the side branch tube 24 fabricated from a flexible, thin-walled metal (preferably steel) tube 24B (or a flat-wire helical coil) either of which could be covered with a thin-walled plastic tube 24A. Such a construction allows the stent 20 to be crimped onto the balloon 23 without closing the interior lumen of the side branch tube 24. Such a design could be used to assure a free sliding motion of the side branch tube 24 over the side branch guide wire 32. It is also envisioned that the side branch tube 24 could be fabricated from a single material being either metal or plastic.

FIGS. 2 and 4 illustrate that the main guide wire 31 could be larger in diameter (or it could be the same diameter) as compared to the side branch guide wire 32. Specifically, one would typically use a main guide wire 31 having a diameter of 0.014 inches and a side branch guide wire having a diameter of either 0.010 or 0.014 inches.

The distal portion of stent delivery catheter system 10 can be placed into an arterial bifurcation using the following procedure:

(a) The guide wire 31 is advanced (using any conventional insertion method) through the main artery 1 and into the main artery continuation 2.

(b) The side branch guide wire 32 is then advanced (using any conventional insertion method) through the main artery 1 and into the side branch 3.

(c) The proximal end of the guide wire 31 (which proximal end lies outside the patient's body typically at the groin) is then fed into the distal end of the inner shaft 26, and the proximal end of the guide wire 32 (which proximal end of the guide wire 32 also is situated outside the patient's body) is then fed into the distal end of the side branch tube 24.

(d) The stent delivery catheter system 10 is then advanced (typically within a guiding catheter) over the guide wires 31 and 32.

(e) As the crotch point 27 which is the intersection of the side branch tube 24 with the balloon 23 approaches the arterial bifurcation saddle point 4, the inner shaft 26 with the distal portion of the balloon 23 and the stent distal portion 22 are all guided into the artery continuation 2 while at the same time, the side branch tube 24 is guided into the side branch 3. The torque acting between the stent distal portion 22 and side branch tube 24 causes the distal portion of the stent delivery catheter system 10 to rotate to the correct angular orientation as shown in FIGS. 1 and 3.

(f) When the forward motion of the crotch point 27 is stopped by being advanced against the saddle point 4, the distal portion of the stent delivery catheter system 10 will have the proper angular orientation and the correct longitudinal placement.

(g) The balloon 23 can then be inflated by conventional means that are well known in the field of balloon angioplasty thereby radially expanding the stent 20 to form the deployed stent 20' as shown in FIG. 3.

(h) The balloon 23' is then deflated and the unique design balloon angioplasty catheter of the stent delivery catheter system 10 is then pulled back out of the patient's body leaving the deployed stent 20' in place.

(i) The main guide wire 31 can then be removed or it could remain in place during one or more additional intravascular procedures. One such procedure would be to place a non-compliant balloon of a balloon angioplasty catheter (not shown) into the stent distal portion 22' so as to further expand that distal portion of the stent 20' for a better match of the deployed stent diameter with the actual diameter of the artery continuation 2. A second such procedure would be to place a non-compliant balloon of a balloon angioplasty catheter (not shown) into the stent proximal portion 21' so as to further expand that proximal portion of the stent 20' for a better match of the deployed stent diameter with the diameter of the main artery 1.

(j) Typically (but not always) after the main guide wire 31 is removed, a stent mounted on a separate stent delivery catheter is then advanced over the side branch guide wire 32 and that stent 40 is placed at the origin of the side branch 3. The stent 40 is shown deployed into the side branch 3 in FIG. 5.

(k) The side branch guide wire 32 is removed from the patient's body.

Figure 5:
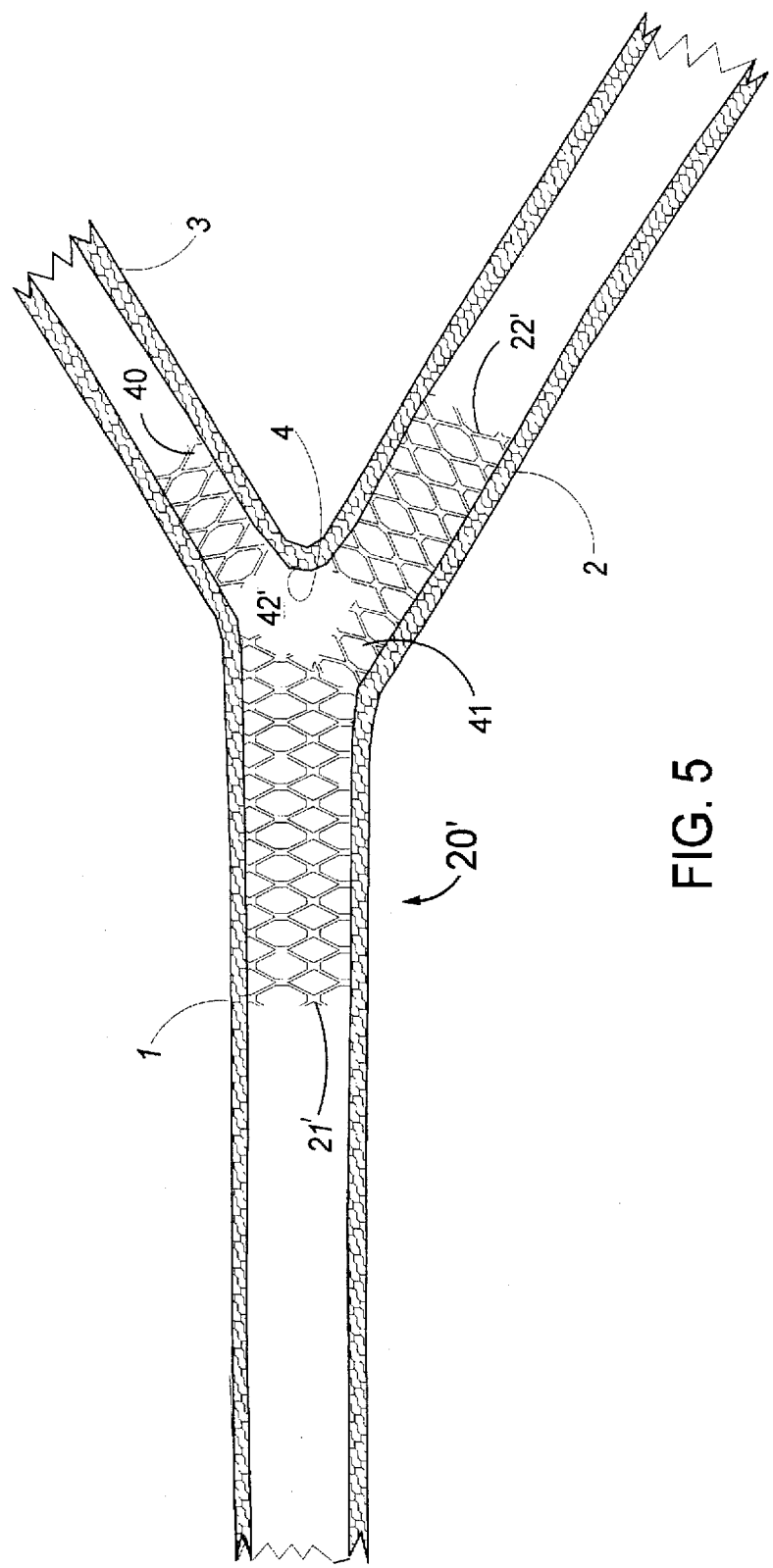
FIG. 5 shows a longitudinal cross section of the bifurcation stent after it has been deployed and also a second stent that has been placed in the side branch opposite the main artery continuation.

It can be seen from FIG. 5 that one or more joining sections 41 join the stent proximal portion 21' to the stent distal portion 22'. The open space 42' is a very important aspect of this stent design because it is this open space 42' through which (after the stent 20' is deployed) the blood can flow into the side branch artery 3, and also other stents (such as the stent 40 of FIG. 5) can be advanced on a stent delivery catheter through the open space 42' and over the side branch guide wire 32 and into the side branch artery 3. The longitudinal length of the opening 42' should be at least 1.0 mm and preferably about 2.0 mm.

Figure 6:
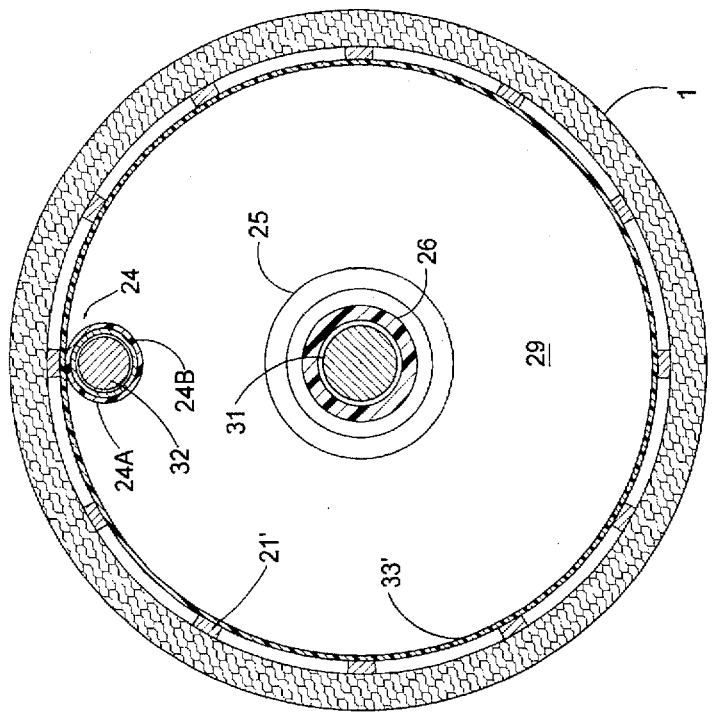
FIG. 6 shows an alternative embodiment of the invention wherein the side branch tube lies within a proximal portion of the inflatable balloon.

FIG. 6 illustrates an alternative embodiment 33' of the balloon 23'. Specifically, FIG. 6 shows the side branch tube 24 placed within the balloon 33'. For this design, the side branch tube 24 would be sealingly joined to the balloon 33' both at a central attachment point of the balloon 33' and at the proximal end of the balloon 33'. The central attachment point of the balloon 33' is equivalent to the crotch point 27 as shown in FIGS. 1 and 3. FIG. 6 also shows the side branch tube 24 consisting of a metal tube 24B and a plastic tube 24A, the side branch guide wire 32, the main guide wire 31, the stent proximal portion 21' and the outer shaft 25. It is also envisioned that the thin-walled flexible metal tube 24B could be in the form of a wire mesh cylinder that is coated on its interior or exterior, either or both, with a plastic covering which all together form the side branch tube 24.

Although this invention shows the central attachment or crotch point 27 to be located at or near a longitudinal mid-point of the balloon 23, the side branch tube 24 could emanate from the outer surface of the balloon 23 at any point which lies within the central 70% of the stent's length. For example, if the stent 20 had a length of 10 mm, the crotch point 27 could lie within a section that is inside a distance of 1.5 mm from either end of the stent. Furthermore, although the stent proximal portion 21 and stent distal portion 22 are shown in FIG. 1 to be nearly equal in length (i.e., a ratio of 1:1), in fact stent length ratios as extreme as 1:5 or 5:1 could be used for the treatment of stenoses that have greatly different lengths in the main artery 1 as compared to the artery continuation 2. For example, in FIG. 5, the stent distal portion 22' is shown to be approximately one-half the length of the stent proximal portion 21'.

It is envisioned that two separate stents not connected by struts or joining sections 41 could be placed on the balloon 23. For example, a stent like the stent proximal portion 21' could be placed on a proximal portion of the balloon 23 and a separate stent like the stent distal portion 22' could be placed on a distal portion of the balloon 23. Furthermore, an inflatable balloon of a uniform diameter could be used for placing a single bifurcation stent or two separate stents into the arteries 1 and 2. A separate non-compliant balloon at a distal portion of a balloon angioplasty catheter when inflated could then be used to further increase the diameter of the stent portion lying within the main artery 1 or within the main artery continuation 2.

It should be understood that the balloon angioplasty catheter on which the stent 20 is mounted could be an "over-the-wire" design which is characterized by having the guide wire 31 exit from the proximal end of the balloon angioplasty catheter at a point that lies outside the patient's body. Alternatively, the balloon angioplasty catheter on which the stent 20 is mounted could be a "rapid exchange" design in which the main guide wire 31 exits the balloon angioplasty catheter at a point that lies within 30 cm distal from the proximal end of the balloon 23. Both "over-the-wire" and "rapid exchange" balloon catheters are well known in the art of balloon angioplasty.

It is envisioned that the most frequent use for this type of stent will be at the bifurcation of the coronary left anterior descending artery with its diagonal branch. At this bifurcation the bifurcation angle $\alpha$ typically lies between 30° and 60°. For implantation at this site, the deployed diameter of the stent distal portion 22' should be between 2.0 and 3.5 mm, and the deployed diameter of the stent proximal portion 21' should lie between 2.5 and 4.0 mm. Another site that could be usefully treated with such a bifurcation stent is at the intersection of the coronary left circumflex artery with its obtuse marginal branch. At this site, the bifurcation angle $\alpha$ typically lies between 45° and 70°. For this use, deployed diameters of the proximal and distal portions of the stent 20' would be similar to the diameters described above for use at the diagonal branch bifurcation of the left anterior descending artery.

It is also envisioned that the stent delivery catheter system 10 described herein could be used successfully at bifurcation angles $\alpha$ as large as 90°, and possible as large as 110°. It is probable that the present invention could be used at angles $10° \leq \alpha \leq 110°$ which angles constitute essentially all arterial side branches and bifurcations.

It is important to note that this invention does not consider a bifurcated balloon that would place a bifurcated stent into both the artery continuation 2 and the side branch 3 as well as the main artery 1. Such a stent configuration would essentially double the diameter of the pre-deployed stent over its entire distal length. This could increase the pre-deployed stent diameter to be greater than 2 mm in diameter which would require a larger diameter guiding catheter for insertion in a coronary artery. The present invention can be accomplished with an outside diameter of less than 2 mm which can more easily be placed in a coronary artery.

It should also be noted that the proximal end of the side branch tube 24 could extend in a proximal direction for the entire length of the balloon angioplasty catheter. Or the outer shaft 25 could be made into a dual lumen tube and have the side branch guide wire first pass through such a second lumen and then enter into the proximal end of the side branch tube 24.

It is also important to note that the operator (typically an interventional cardiologist) who would place this stent delivery catheter system 10 can be assured of proper placement of the side branch tube 24 when he observes by fluoroscopy that the side branch tube 24 and side branch guide wire 32 are parallel to the main guide wire 31 as they lie in the main artery 1 without having any intersection point of the main guide wire 31 and the side branch guide wire 32.

As described in U.S. Pat. No. 5,059,166, which is included herein by reference, the inclusion of a radioisotope into the metal of the stent can prevent the growth of proliferative tissue into the lumen of the stent. Therefore, it is also envisioned that this bifurcation stent could have a radioisotope included into the metal of the stent or placed onto the stent's surface. Experience has shown that such a radioisotope stent is optimally a beta-particle emitter and the best of these uses the isotope phosphorous-32 to make the stent radioactive.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A stent delivery catheter system including a stent for insertion at an arterial bifurcation or arterial side branch, the system comprising:

a first guide wire adapted to be inserted through a main artery and into a continuation artery of that main artery;

a second guide wire adapted to be inserted through the main artery and into a side branch artery of the main artery, the side branch artery and the continuation of the main artery forming an arterial bifurcation therebetween;

a balloon angioplasty catheter having an inner shaft which has a distal end and also an inflatable balloon located at a distal section of the balloon angioplasty catheter, the inflatable balloon having a proximal end and a distal end, the distal end of the balloon being sealingly joined to the distal end of the inner shaft, the inner shaft being adapted to be slidingly advanced over the first guide wire;

a side branch tube being joined to the balloon near the balloon's proximal end and also being joined to the balloon at a central attachment point which is near the longitudinal center of the balloon from which central attachment point the side branch tube extends for a length of greater than 1 mm in a distal direction free from attachment to the balloon, the side branch tube having a proximal portion and a distal portion and being adapted to be slidingly advanced over the second guide wire, and, an expandable stent having a proximal portion and a distal portion and having an open space therebetween through which open space the side branch tube projects in a distal direction, the proximal portion of the side branch tube lying within the proximal portion of the stent and the distal portion of the side branch tube lying outside the distal portion of the stent.

2. The stent delivery catheter system of claim 1 wherein the balloon when expanded has a uniform outer diameter.

3. The stent delivery catheter system of claim 1 wherein the balloon when expanded has a proximal portion that has a first and larger diameter and a distal portion which has a second and smaller diameter.

4. The stent delivery catheter system of claim 1 wherein the side branch tube extends for a length of at least 10 mm beyond the central attachment point of the balloon to the side branch tube.

5. The stent delivery catheter system of claim 1 wherein the side branch tube lies entirely outside of the outer surface of the balloon.

6. The stent delivery catheter system of claim 1 wherein some length of the side branch tube lies within the balloon.

7. The stent delivery catheter system of claim 1 wherein the side branch tube includes a thin-walled, flexible metal tube adapted to slide over the side branch guide wire, the metal tube retaining a generally circular lumen after the stent is crimped onto the balloon.

8. The stent delivery catheter system of claim 1 wherein the balloon angioplasty catheter has a proximal end and is the "over-the-wire" design which has the first guide wire exit the balloon angioplasty catheter at the balloon angioplasty catheter's proximal end.

9. The stent delivery catheter system of claim 1 wherein the balloon angioplasty catheter is of a "rapid exchange" design that has the first guide wire exit from the balloon angioplasty catheter within a region that is within 30 cm in a proximal direction from the proximal end of the balloon of the balloon angioplasty catheter.

10. The stent delivery catheter system of claim 1 wherein the opening between the stent's proximal portion and the stent's distal portion has a length in the longitudinal direction of at least 1.0 mm.

11. The stent delivery catheter system of claim 1 wherein the stent's proximal portion and distal portion are mechanically joined together by means of one or more stent joining sections.

12. The stent delivery catheter system of claim 1 wherein the stent's proximal portion is separate and distinct from and is free from any metal joining section attachment to the stent's distal portion thereby forming two separate stents.

13. The stent delivery catheter system of claim 1 wherein the stent is radioactive.

14. The stent delivery catheter system of claim 13 wherein the radioactive stent emits more energy from beta particles as compared to alpha or gamma emission.

15. The stent delivery catheter system of claim 14 wherein the source of the beta-particles is the radioisotope phosphorous-32.

16. A method for the treatment of one or more stenoses located at an arterial bifurcation, the method comprising the following steps:

(a) placing a main guide wire which has a proximal end though a main artery and into a main artery continuation;

(b) placing a side branch guide wire which has a proximal end through the main artery and into a side branch artery which side branch artery and main artery continuation form a bifurcation of the main artery, the point at which the main artery is joined to the side branch artery being a saddle point;

(c) placing the proximal end of the main guide wire through the distal end of an inner shaft of a balloon angioplasty catheter which includes a balloon located at a distal section of the balloon angioplasty catheter;

(d) placing the proximal end of the side branch guide wire through the distal end of a side branch tube which side branch tube emanates in a distal direction from the balloon of the balloon angioplasty catheter at a crotch point which is a longitudinally centrally located point of the balloon;

(e) advancing the balloon angioplasty catheter including the side branch tube until the crotch point is situated at the saddle point of the arterial bifurcation;

(f) inflating the balloon of the balloon angioplasty catheter so that a stent mounted onto the exterior surface of the balloon is forced radially outward against the interior surfaces of the main artery and the main artery continuation;

(g) deflating the balloon of the balloon angioplasty catheter;

(h) removing the balloon catheter from the patient's body.

17. The method of claim 16 including the steps of advancing another balloon angioplasty catheter over the main guide wire and inflating a balloon within that portion of the stent that has been placed in the main artery so as to further expand that portion of the stent.

18. The method of claim 16 including the steps of removing the main guide wire from the patient's body and advancing a second balloon angioplasty catheter with a second stent mounted onto the balloon of the second balloon angioplasty catheter over the side branch guide wire and then inflating the balloon of the second balloon angioplasty catheter so as to deploy the second stent against the interior surfaces of the side branch artery and then deflating the balloon and then removing the second balloon angioplasty catheter and the side branch guide wire from the patient's body.

19. The method of claim 16 including the steps of removing the main guide wire and the side branch guide wire.

* * * * *